United States Patent [19]
Ben-Amotz et al.

[11] Patent Number: 5,948,823
[45] Date of Patent: Sep. 7, 1999

[54] IRRADIATION PROTECTION METHOD

[75] Inventors: Ami Ben-Amotz, Savyon; Zeev Weshler, Jerusalem; Shaul Yatziv, Jerusalem; Mordechai Sela, Jerusalem, all of Israel

[73] Assignees: Hadasit Medical Research Services & Development Company Ltd., Jerusalem, Israel; Nikken Sohonsha Corporation, Gifu, Japan

[21] Appl. No.: 08/925,657

[22] Filed: Sep. 9, 1997

[30] Foreign Application Priority Data

Sep. 9, 1996 [IL] Israel ......................................... 119224

[51] Int. Cl.$^6$ .......................... A61K 31/015; A61K 35/78
[52] U.S. Cl. .......................................... 514/763; 424/195.1
[58] Field of Search ............................ 514/763; 424/195.1

[56] References Cited

U.S. PATENT DOCUMENTS

| | | |
|---|---|---|
| 4,511 | 3/1846 | Avron et al. . |
| 4,199,895 | 4/1980 | Avron et al. ................................. 47/1.4 |
| 5,310,554 | 5/1994 | Haigh ........................................ 424/439 |

FOREIGN PATENT DOCUMENTS

| | | |
|---|---|---|
| WO/9303720 | 3/1993 | WIPO . |
| WO/9324454 | 12/1993 | WIPO . |

OTHER PUBLICATIONS

WPI Abstract Acc. No. 94–193711 & FR 2698268 A1.
WPI Abstract Acc. No. 97–416929 & DE 19605659A1.
BIOSIS Abstract Acc. No. 94:164651 American Journal of Clinical Nutrition 59(2), (1994), pp. 58–61.
EMBASE Abstract Acc. No. 94:35722 Byull. Eksp. Biol. Med., (1993) 116 (10), pp. 370–374.
BIOSIS Abstract Acc. No. 93:77497 Biosis Vopr Pitan 0 (1992), (2),pp. 370–374.
CAPLUS Abstract No. 102:20438 & JNCI (1984), 73(5) pp. 1167–1177.
CAPLUS Abstract No. 99:136176 & JNCI (1983), 71(2) pp. 409–417.
Kuten, A. et al., Int. J. Radiation Oncology Bio. Phys., 12:401–405, 1986.
Burton, G.W. and Ingold, K. U. β–carotene: an unusual type of lipid antioxidant, Science, 224:569–573, 1989.
Dunaliella: Physiology, Biochemistry, and Biotechnology, Ed. Avron, M. and Ben–Amotz, A. 9:206–16, 1992.
Bioavailability of a Natural isomer mixture as compared with synthetic al–trans beta–carotene in rats and chicks, J. Nutrition, 119:1013–1019, 1989.
Bioavailability of a natural isomer mixture compared with synthetic all–trans β–carotene in human serum, Am. J. Clin. Nutr., 63:729–734, 1996.
Ben–Amotz, A. Katz, A. and Avron, M.J. Phycology, 18:529–537, 1982.
"Effect of Dietary Supplementation of Different β–Carotene Isomers on Lipoprotein Oxidative Modification," Yishai Levy, MD et al., *Journal of Nutritional & Environmental Medicine* (1995), 5 pp. 13–22.
"β–Carotene and CNS oxygen toxicity in rats," Noemi Bitterman et al., *Israeli Naval Hyperbaric Institute and Israel Oceanographic and Limnological Research, Haifa 31080, Israel*, 1984.
"The influence of feed high in synthetic beta–carotene on the survival rate of gamma–irradiated CBA mice" V.K. Lemberg et al., *Radiobiologiya* (1990), 30(6), 843–4 (Abstract).

(List continued on next page.)

*Primary Examiner*—Phyllis G. Spivack
*Attorney, Agent, or Firm*—Birch, Stewart, Kolasch & Birch, LLP

[57] ABSTRACT

A method of protecting a mammal from the detrimental effects of irradiation is disclosed. The method comprises administering an effective amount of a substantially crude Dunaliella algae preparation to the mammal.

10 Claims, 4 Drawing Sheets

OTHER PUBLICATIONS

"Radioprotective action of natural carotene–containing preparatons: research on karotinil in white rats," M.M. Vilenchik et al., *Radiobiologiya* 28(4): 542–4 1988 Jul.–Aug. (Abstract).

"Modification of the body's resistance to acute ionizing radiation by synthetic beta–carotene," I.K. Beliaev et al., *Vopr Med Khim,* 38(6):39–42 1992 Nov–Dec (Abstract).

"Prospects of the use of beta–carotene enriched food products in the prevention and therapy of radiation injuries," I.K. Beliaev et al., *Vopr. Pitan,* (2):58–61 1992 Mar.–Apr. (Abstract).

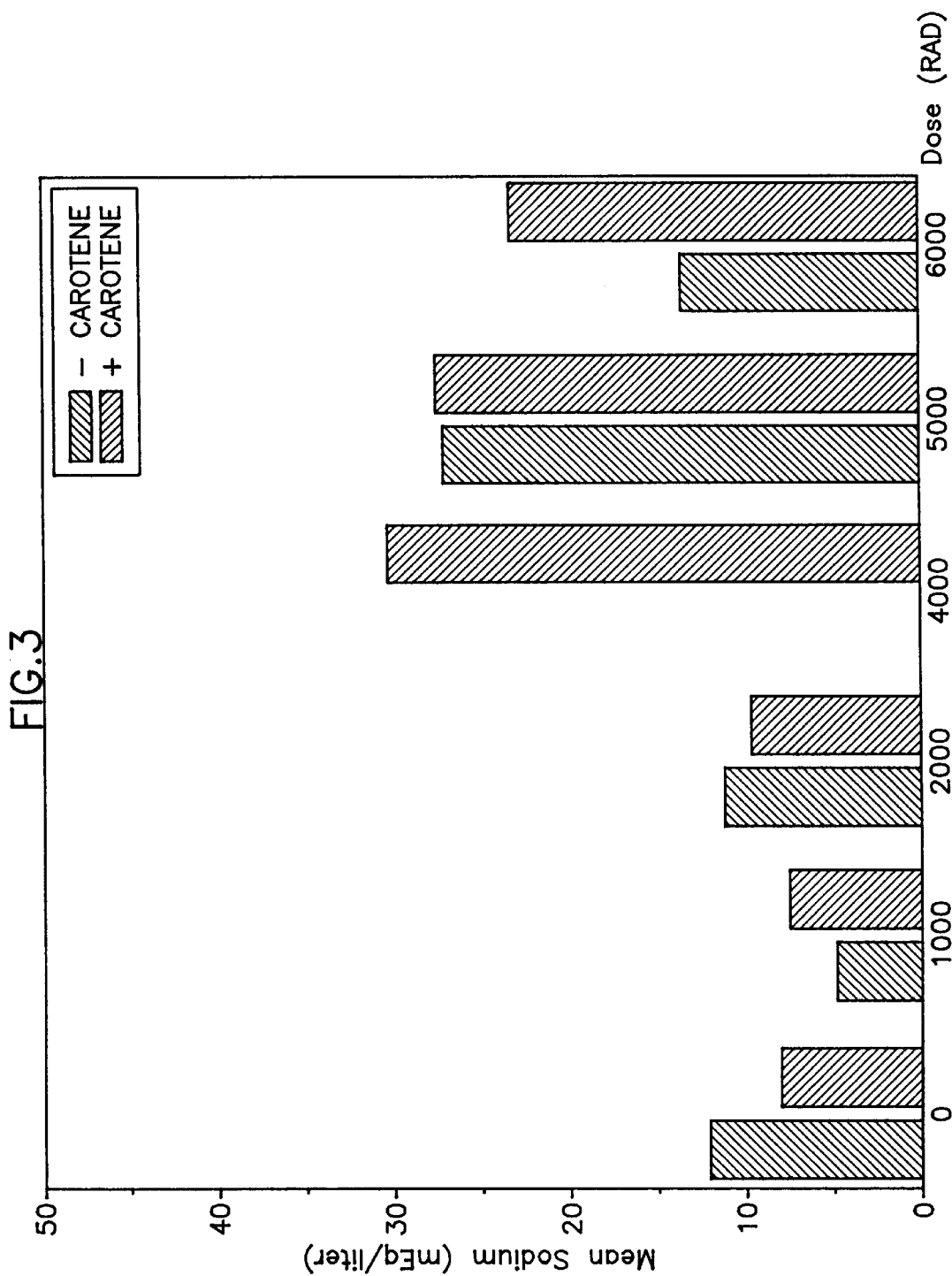

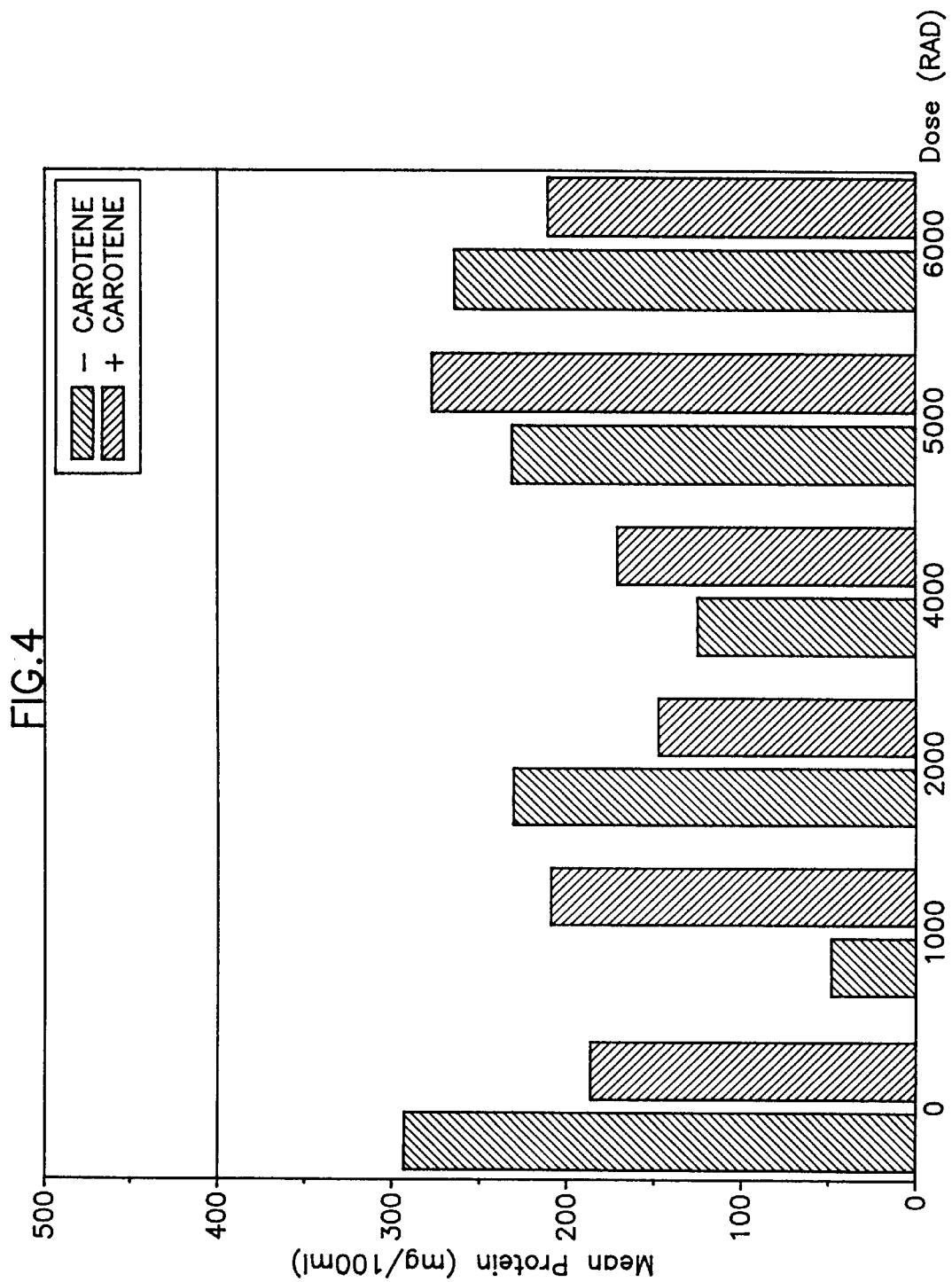

IRRADIATION PROTECTION METHOD

FIELD OF THE INVENTION

The present invention relates to a method for protecting mammals from the detrimental effects of irradiation.

PRIOR ART

The following is a list of prior art references believed to be pertinent as a background to the present invention:
1. Kuten, A., et al. Oral side effects of head and neck irradiation: correlation between clinical manifestations & laboratory data. *Int. J. Radiation Oncology Boil Phys.*, 12:401–405, 1986.
2. Burton, G. W. and Ingold, K. U. β-carotene: an unusual type of lipid antioxidant. *Science*, 224:569–573, 1989.
3. Seifter E., Rettura G., Padawer J., Stratford F., Goodwin P., Levenson S. Supplemental vitamin A and beta-carotene reduce morbidity and mortality in mice subjected to partial or while body irradiation. In: The first conference on radioprotectors and anticarcinogens, Gaithersburg, Md., National Bureau of Standards, Jun. 21–24, 1982, Abstract #44.
4. Ben-Amotz, A. and Shaish, A. β-Carotene Biosynthesis in *Dunaliella: Physiology, Biochemistry and Biotechnology*. Ed. Avron, M. and Ben-Amotz, A., 9:206–16, 1992.
5. U.S. Plant Pat. No. 4,511, issued Mar. 18, 1980.
6. U.S. Pat. No. 4,199,895, issued Apr. 29, 1980.
7. Ben-Amotz, A., Mokady, S., Edelstein, S. and Avron, M. Bio-availability of a natural isomer mixture as compared with synthetic all-trans beta-carotene in rats and chicks, *J. Nutrition*, 119:1013–1019, 1989.
8. Ben-Amotz, A. and Levi, Y. Bioavailability of a natural isomer mixture compared with synthetic all-trans μ-carotene in human serum, *Am. J. Clin. Nutr.*, 63:729–734, 1996.
9. Ben-Amotz, A., Katz, A. and Avron, M. *J. Phycology*, 18:529–537, 1982.

The above prior art references will be acknowledged in the text by indicating their number from the above list (within brackets).

BACKGROUND OF THE INVENTION

Exposure to radioactive radiation of various levels and types is becoming increasingly common. For example, whole body irradiation is utilized to induce immunosuppression in patients with leukemia or autoimmune disease. Various malignancies such as those in the head-neck region are often treated by radiotherapy.

In addition, individuals are occasionally exposed to radiation from their environment. During the past 50 years four major industrial radioactive accidents were reported in Kistym (USSR) and Wind-Scale (England) in 1957, Three Mile Island (USA) in 1979 and in Chernobyl (USSR) in 1986. These accidents (and especially the last) resulted in widespread exposure to various levels of radioactivity.

It is well known that irradiation often leads to functional alterations in organs and subsequent development of various disorders and diseases, especially malignant diseases. For example, irradiation of the head and neck regions causes significant damage to structures and functions in the oral cavity[1]. Leukemia, thyroid, breast, lung and gastrointestinal cancers are the most frequent radiation induced diseases. The role of free radicals in carcinogenesis, radiation induced damages and immunodeficiency is well known. The reactive oxygen species, superoxide hydrogen peroxide and hydroxyl free radicals are generated in vitro as normal metabolites. Oxidative DNA damage is a major cause of endogenous mutations. The fraction of reversible and repairable radiation-induced damages may be increased by administrating radioprotective and cancer preventing agents such as antioxidants.

Beta-carotene (the precursor of vitamin A) is one of the most effective substances known to quench the activity of exited and singlet oxygen, and has been reported to be a potent free radical quencher, singlet oxygen scavenger and lipid antioxidant[2]. Supplemental vitamin A as well as β-carotene diminish the toxicity due to local X-ray or whole body irradiation[3]. Both of them also inhibit carcinogenesis caused by some chemicals or UV irradiation. In animal models as well as human pre malignant diseases of the oral cavity, β-carotene is able to reduce the incidence of malignant diseases of the oral cavity, to reduce the incidence of malignant transformation and to cure the leukoplakia or papillomas.

In contrast to other retinoids, β-carotene does not influence the plasma lipid level and is not toxic, qualities which makes it an excellent candidate for chemoprevention of cancer.

Two strains of Dunaliella, a unicellular, biflagellate, wall-less green alga, are capable of producing very large amounts of β-carotene, *Dunaliella salina* Teod. and *Dunaliella bardawil*[4]. *D. bardawil* is a halotolerant alga whose β-carotene content comprises about 50% all-trans-β-carotene with the remainder composed mostly of 9-cis-β-carotene and a few other β-carotene isomers[5]. A process has been described for cultivating *D. bardawil* so as to obtain algae containing up to about 5% by weight of β-carotene[6]. Later developments of the process increased the percentage to more than 8%[4,9]. It has been shown that the natural isomer mixture of β-carotene which is accumulated in the alga *Dunaliella bardawil* is accumulated in fatty tissues of rats and chicks to an extent which is about 10 fold higher than that observed by feeding the synthetic all-trans β-carotene[7].

WO 93/24454 describes a carotenoid composition derived from Dunaliella algae in which the β-carotene content is predominantly 9-cis β-carotene. There is no mention of any medical applications.

Various carotenoid-enriched Dunaliella commercial products are available such as Betatene™ (produced by the Henkel Corp., Germany) and Nutrilite™ (Amway, Inc., U.S.A.). These products are oil extracts of carotenoids from Dunaliella.

BRIEF SUMMARY OF THE INVENTION

It is an object of the present invention to provide a method for protecting mammals from the detrimental effects of irradiation.

It is another object of the present invention to provide a medicament for protecting mammals from the detrimental effects of irradiation.

The present invention provides by one of its aspects, a method for protecting a mammal from the detrimental effects of irradiation comprising administering to the mammal an effective amount of an active ingredient. In accordance with another aspect of the invention there is provided a medicament for use in protecting mammals against the detriment effect of irradiation, comprising an effective amount of an active ingredient.

The active ingredient in accordance with one embodiment is a natural β-carotene. In accordance with another embodiment of the invention, the active ingredient is a substantially crude Dunaliella algae preparation, typically dried Dunaliella algae. The Dunaliella algae are preferably *Dunaliella bardawil.*

Use of an essentially crude Dunaliella algae preparation is generally preferred in accordance with the invention.

Also provided by the invention is use of said active ingredient for the preparation of a medicament for use in protecting mammals against the detrimental effects of irradiation.

Said mammals are preferably humans.

The effective amount should be understood as an amount of said active ingredient which is sufficient to achieve the desired therapeutic effect, i.e. protection of the mammal from the detrimental effect of irradiation. The effective amount depends on the various factors including the type of irradiation to which the individual is exposed, i.e. whether it is an irradiation within the form of therapy or whether one resulting from environmental exposure, e.g. in the case of a nuclear disaster; on the administration regimen, e.g. whether the preparation is given once or several times over a period of time; etc. The artisan should have no difficulties, by minimal experiments, to determine the effective amount in each case.

The method of the invention is based on the surprising discovery that β-carotene can be used to prevent the detrimental effects of irradiation in humans. In particular, the therapeutic qualities of β-carotene are maximized when administered in its natural state in the form of dry powdered Dunaliella algae. This is supported by the results of a recent study which showed the superior bioavailability of natural β-carotene over the synthetic product, which consists of the all-trans isomer only(8). The use of whole algae containing all of its biochemical components is believed to be preferable over the use of an oil extract, as in the commercial products described above.

The medicament can be administered prior to, during or subsequent to the irradiation. In a preferred embodiment, the medicament is in the form of a dry powder enclosed in a capsule.

BRIEF DESCRIPTION OF THE DRAWINGS

The present invention will be better understood from the following detailed description of preferred embodiments, taken in conjunction with the following drawings in which:

FIGS. 2 and 3 illustrate the levels of potassium and sodium concentrations, respectively, in the saliva as a function of radiation dose; and FIG. 4 illustrates the level of protein concentration in the saliva as a function of radiation dose.

DETAILED DESCRIPTION OF PREFERRED EMBODIMENTS

All of the studies described below employed capsules containing Dunaliella powder prepared as follows.

*Dunaliella bardawil* (hereinafter "Db") was grown and cultivated in large body open salt water ponds of 50,000 m$^2$ to obtain algae comprising 8% by weight of β-carotene (hereinafter "BC") at an approximately 1:1 ratio of all-trans and 9-cis BC (4,9). The algae were harvested by dissludging centrifuges into a concentrated paste. The paste was washed to remove the salt and sterilized, and then spray dried to yield Db powder comprising approximately 8% BC and less than 5% moisture. The powder was packaged in capsules of 250 mg algae containing 20 mg of BC each together with all of the natural components of the algae. The BC of the capsules retains the original 1:1 ratio of isomers. The capsules are packaged in vacuum closed blisters which have a shelf life of up to three years.

EXAMPLE 1

Patients undergoing local radiation therapy for neoplastic diseases in the head and neck regions took two capsules of Db per day for a period of 6–10 days prior to being irradiated once a day. The capsules contained 19±1 mg of BC each.

40 patients received BC capsules while 20 patients acted as a control. The patients received at least two levels of radiation. Radiation-induced damage to the salivary glands was followed with respect to: (1) a decrease in the level of saliva secretion; and (2) an increase in electrolyte and protein concentration in the saliva.

Results

Figure 1:
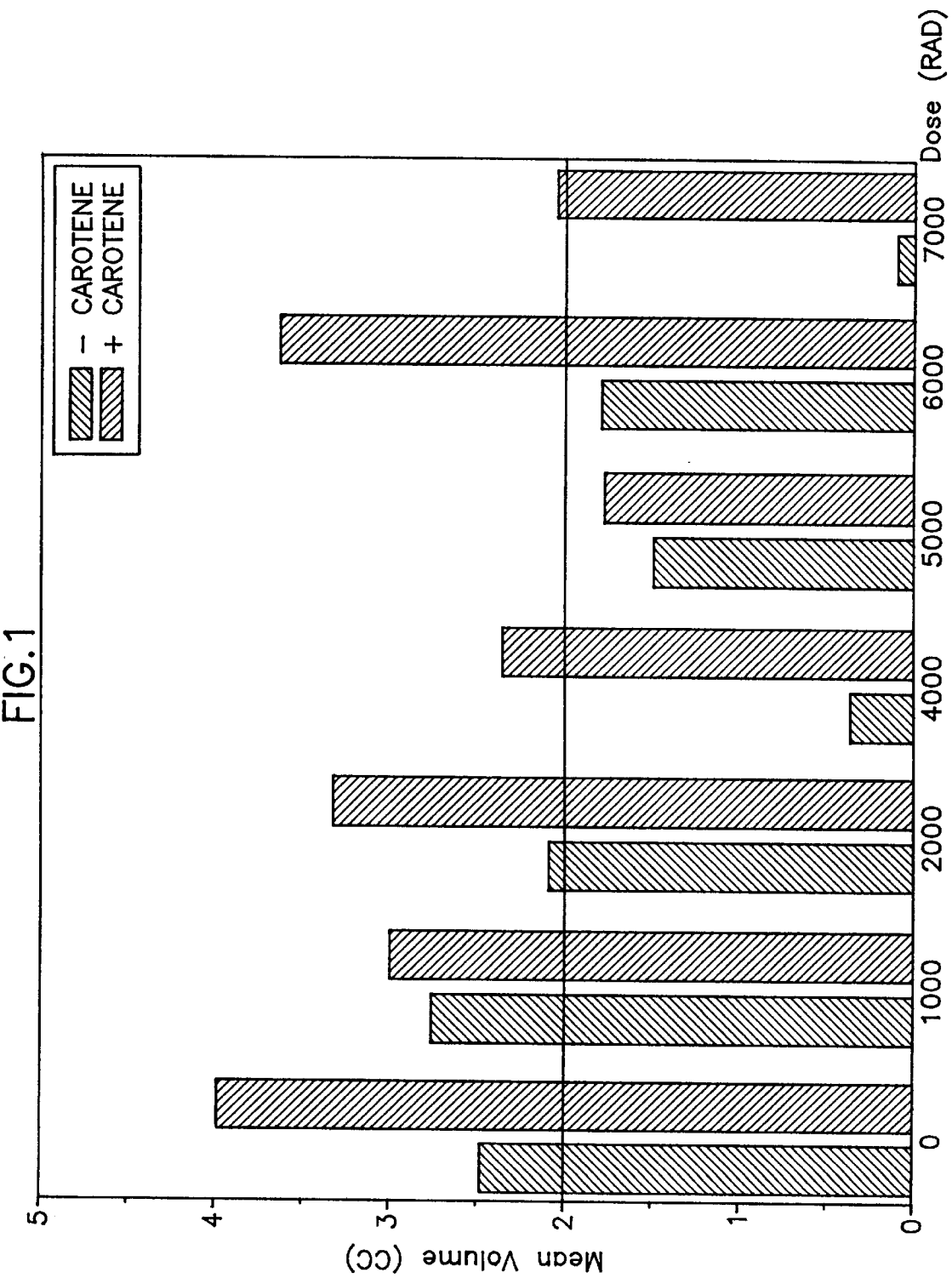
FIG. 1 illustrates the level of saliva secretion as a function of radiation dose (the horizontal line indicates the normal volume of saliva)
Figure 2:
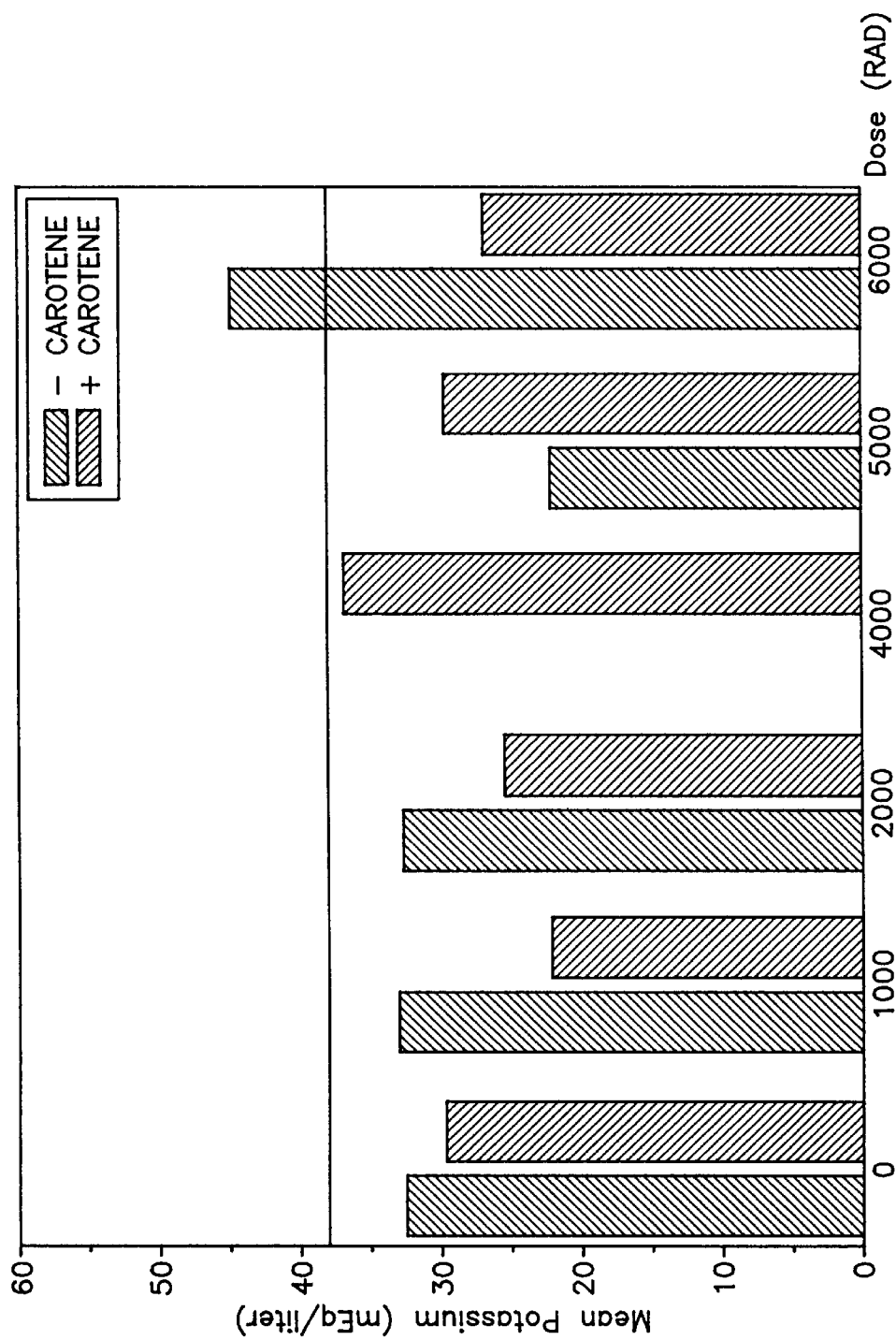

From the results given in FIGS. 1–4 it can be seen that preventive administration of natural caritenoids decreased the local tissue damage in the irradiated areas. Clinical follow-up studies in these patients (not shown) revealed that improved recovery of the salivary glands was seen in the patients receiving BC before and during treatment.

In another group, an improvement in the mucosal inflammatory reaction to irradiation was observed. In both groups, no toxic effects were noticed.

EXAMPLE 2

About 1000 children who were exposed to radiation in the Chernobyl area following the reactor explosion in 1986, and who arrived in Israel between 1990–1993, were examined by a multidisciplinary team of physicians from the Hadassah Medical Organization, Jerusalem. They came from very contaminated towns and settlements: Gomel, Mozyr, Vetka, Kalinkovich and Rechitza, and from low contaminated zones like Kiev, Zitomir, Korostyn etc.

The preliminary results of those examinations are presented in the Table I and II.

TABLE I

Diseases among children from Chernobyl area (1990–1991)

| Diseases | Total | % |
| --- | --- | --- |
| Malignant diseases | | |
| Leukemia and thyroid carcinoma | 2 | 0.5 |
| Endocrine disorders | | |
| Goiter unspecified | 127 | 38.7 |
| Nodular Goiter (ultrasound verified) | 116 | 35.4 |
| 6 cases (14.6%) out of 46. Includes: | | |
| Nodular goiter solid - 5 cases and | | |
| 1 cystic goiter | | |
| Diseases of the eyes (out of 204 children) | 115 | 56.4 |
| Dry eye syndrome | 87 | 42.6 |
| Inflammatory diseases | 41 | 20.0 |
| Psychological disorders | 39 | 12.5 |
| Disorders of the Digestive System | 23 | 7.0 |

TABLE I-continued

Diseases among children from Chernobyl area (1990–1991)

| Diseases | Total | % |
|---|---|---|
| Disorders of the Respiratory System | 75 | 22.9 |
| Disorders of the Genitourinary System | 30 | 9.1 |
| All diseases were examined in 328 children | | |

TABLE II

Diseases among children from Chernobyl area (1990–1993)

| Disorders | High contaminated area >5 Ci/Km$^2$ | | Low contaminated area <5 Ci/Km$^2$ | | Background irradiation | |
|---|---|---|---|---|---|---|
| | Total | % | Total | % | Total | % |
| BOYS | 154 | | 106 | | 64 | |
| Neoplasms | | | 3 | 2.83 | | |
| Endocrine Disorders | 47 | 30.52 | 19 | 17.92 | 7 | 10.94 |
| Mental Disorders | 14 | 9.09 | 30 | 28.30 | 14 | 21.88 |
| Circulatory System Disorders | 5 | 3.25 | 5 | 4.72 | 2 | 3.13 |
| Respiratory System Disorders | 20 | 12.99 | 32 | 30.19 | 14 | 21.88 |
| Digestive System Disorders | 2 | 1.30 | 28 | 26.42 | 7 | 19.94 |
| Eye Diseases | 45 | 29.22 | 14 | 13.21 | 10 | 15.63 |
| GIRLS | 157 | | 148 | | 80 | |
| Endocrine Disorders | 67 | 42.68 | 42 | 28.38 | 16 | 20.00 |
| Mental Disorders | 24 | 15.29 | 17 | 11.49 | 8 | 10.00 |
| Circulatory System Disorders | 15 | 9.55 | 14 | 9.46 | 6 | 7.50 |
| Respiratory System Disorders | 31 | 19.75 | 48 | 32.43 | 27 | 33.75 |
| Digestive System Disorders | 9 | 5.73 | 37 | 25.00 | 19 | 23.75 |
| Eye Diseases | 76 | 48.41 | 30 | 20.27 | 11 | 13.75 |

Permission for the clinical trial was obtained from the Helsinki Committee. 120 of these children were given 20 mg of BC twice daily (total dose BC 40 mg per day) for a period of three months.

Results

During the experimental period, a significant increase in the level of blood caretenoids was noticed. The blood level of vitamin A, considered to be highly toxic on long term use, was reduced. Similarly, a moderate reduction in blood levels of vitamin E was also noticed. At the end of the three-months experimental period, the vitamin levels returned to their normal values and remained thus thereafter, and no clinical or laboratory side effects were detected.

The tendency of the Chernobyl children to develop infectious diseases decreased by 30%. In addition, a significant increase in their weight was recorded.

From the above results it can be seen that natural BC can be used as a prophylactic tool to prevent short and long term irradiation-induced damage. The natural carotenoids can be administered orally and do not have toxic side effects.

It will be appreciated by persons skilled in the art that the present invention is not limited to what has been thus far described, but rather the scope of the present invention is limited only by the following claims.

We claim:

1. A method of protecting a mammal from the detrimental effects of irradiation comprising administering to said mammal an effective amount of a substantially crude Dunaliella algae preparation.

2. A method according to claim 1, wherein said algae is *Dunaliella bardawil.*

3. A method according to claim 1, wherein said algae preparation comprises the whole algae organism.

4. A method according to claim 1, wherein said algae comprises at least 8%, by weight, of β-carotene.

5. A method according to claim 4 wherein said β-carotene comprises both all-trans β-carotene and cis β-carotene.

6. A method according to claim 1, wherein said preparation is administered prior to irradiation.

7. A method according to claim 1, wherein said preparation is administered concurrently with said irradiation.

8. A method according to claim 1, wherein said preparation is administered subsequent to irradiation.

9. A method according to claim 1, wherein said mammal is a human being.

10. A method according to claim 1, wherein said preparation is in the form of an encapsulated dry powder.

* * * * *